(12) United States Patent
Bandyopadhyay et al.

(10) Patent No.: US 6,967,034 B2
(45) Date of Patent: *Nov. 22, 2005

(54) HERBAL-BASED COMPOSITION FOR TREATING ACUTE AND CHRONIC MYELOID LEUKEMIA

(75) Inventors: Santu Bandyopadhyay, Kolkata (IN); Keshab Chandra Roy, Kolkata (IN); Mitali Ray, Kolkata (IN); Goutam Banerjee, Kolkata (IN); Bikash Chandra Pal, Kolkata (IN); Tanusree Biswas, Kolkata (IN); Samir Bhattacharya, Kolkata (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

This patent is subject to a terminal disclaimer.

(21) Appl. No.: 10/448,398

(22) Filed: May 30, 2003

(65) Prior Publication Data

US 2004/0043086 A1 Mar. 4, 2004

Related U.S. Application Data

(60) Provisional application No. 60/384,163, filed on May 31, 2002.

(51) Int. Cl.$^7$ .............................................. A61K 35/78
(52) U.S. Cl. ...................... 424/769; 424/774; 514/908
(58) Field of Search ................................ 424/769, 774, 424/725; 514/908

(56) References Cited

U.S. PATENT DOCUMENTS

| | | | | |
|---|---|---|---|---|
| 5,389,371 | A | 2/1995 | Shiao | 424/195.1 |
| 5,582,822 | A * | 12/1996 | Brandely et al. | 424/85.2 |
| 6,610,332 | B2 | 8/2003 | Bandyopadhyay et al. | 424/769 |

FOREIGN PATENT DOCUMENTS

| | | |
|---|---|---|
| JP | 401261403 A | 10/1989 |
| JP | 09278666 A | 10/1997 |
| JP | 10077495 A | 3/1998 |
| JP | 11130685 A | 5/1999 |

OTHER PUBLICATIONS

Jain, Rakesh K., Science, 271: 1079–1080. Delivery of molecular medicine to solid tumors.*
Wealth of India, vol. 8, pp. 84–95.
Sengupta et al., Indian Journal of Experimental Biology, (Apr. 2000), vol. 38, 338–342.
Sadasivan et al., Mutation Research, Chromosome–Damaging Effect of Betel Leaf, (1978), vol. 57, pp. 183–185.
Van de Graaff et al., Concepts of Human Anatomy and Physiology, WCB Publishers, (1986) pp. 159, 618, 706–709.
Database WPI, Section CH, Week 199930, Derwent Publications Ltd., London, BG; AN 1999–352797, XP002174279 (JP 11 130685 A).
Database WPI, Section CH, Week 199702, Derwent Publications Ltd., London, BG; AN 1997–017312, XP002174280 (JP 08 283171 A).
Mori H et al., "Carcinogenicity Examination of Betel Nuts and Piper Betel Leaves", Experientia (1979), vol. 35, No. 3, pp. 384–385. ISSN: 0014–4754, XP001008625.
Sawyers Cl., The New England Journal of Medicine, 340 (17): 1330–1340, 1999.
Vitale C, Romagnani C et al. Proc. Natl. Acd. Sci. USA, 96 (26): 15091–15096.
Vitale C et al., Proc. Natl. Acd. Sci. USA, 98 (10): 5764–5769, 2001.
Sievers el, Appelbaum Fr et al. Blood, 93: 3678–3684, 1999.
Ito H et al., Bioorg. Med. Chem. 6(7): 1051–1056, 1998.
Tiyu G, FTIR, Vibrational Spectroscopy, vol. 24, No. 2, 225–231, 2000.
Fung Va, Mutation Research, vol. 204, No. 2, 219–228, 1988.

* cited by examiner

*Primary Examiner*—Michele Flood
(74) *Attorney, Agent, or Firm*—Fitzpatrick, Cella, Harper & Scinto (57) ABSTRACT

A new herbal-based composition and method for treatment of CD33+ acute and chronic myeloid leukemia by *Piper betel* leaf extracts, and to provide a process for the isolation of active fractions from leaves or any other plant parts of *Piper betel* to treat CD33+ AML and CML with a simplified method of isolation of active components from all plant parts of *Piper betel* possessing biological activities relevant to the treatment of CD33+ AML and CML.

6 Claims, 7 Drawing Sheets

HERBAL-BASED COMPOSITION FOR TREATING ACUTE AND CHRONIC MYELOID LEUKEMIA

This application claims benefit of U.S. Provisional Application No. 60/384,163 filed May 31, 2002.

FIELD OF INVENTION

This invention relates to a herbal based composition for treatment of CD33+ acute and chronic myeloid leukemia by *Piper betel* leaf extracts, fractions of *Piper betel* leaf extracts and 3-O-p-coumaryl quinic acid purified from *Piper betel* leaves extract.

BACKGROUND AND PRIOR ART REFERENCES

Mycloid leukemia, both acute (AML) and chronic (CML) are lethal, there is no drug directing towards the destruction of the myeloid cells and these cells poorly respond to chemotherapy, which is always non-specific, thus adversely affecting normal cells. Unique property of the therapy with *Piper betel* components is the killing of myeloid cancer cells by recognizing CD33+ marker on the cell membrane, leaving normal cells without getting affected.

Myeloid leukemia is usually subdivided into two groups: Acute Myeloid Leukemia (AML) and Chronic Myeloid Leukemia (CML). AML is characterized by an increase in the number of myeloid cells in the bone marrow and an arrest in their maturation. In the United States, the annual incidence of AML is approximately 2.4 per 100,000 and it increases progressively with age, to a peak of 12.6 per 100,000 in adults of 65 years age or older. The CML is a malignant clonal disorder of hematopoietic stem cells. The median age at presentation is 53 years, but it occurs at all age groups, including children. The natural history of CML is progression from a benign chronic phase to a rapidly fatal blast crisis within three to five years or even earlier. The prognosis of CML is also poor inspite of vast advancement of clinical medicine (1). CD33 represents a specific and useful marker in the process of myeloid cell differentiation (2). Recent reports suggest that engagement of CD33 by monoclonal antibody induced apoptosis leading to growth inhibition of proliferation of AML and CML cells in vitro (2,3). Exploiting the myeloid specific expression of CD33, humanized anti-CD33 monoclonal antibody conjugated with anti-cancer drug has been tried in AML patients with significant success (4). With the extract from *Piper betel* leaves anti-myeloid activity was claimed earlier (Patent filed no. PCT/INOO/00118 dated Dec. 12, 2000).

Figure 1:
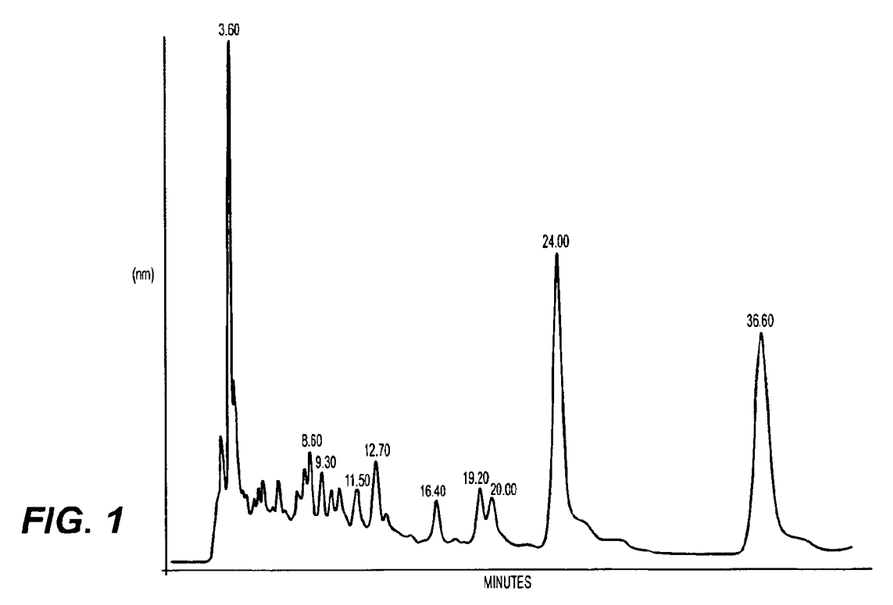
FIG. 1 represents HPLC analysis of fraction E. The first peak having retention time 3.6 min is designated as fraction 1, retention time 24.0 is designated as fraction 9.

Hence, applicant's earlier finding is in directed consonance with the present patent filing on *Piper betel* leaf extract, fractionated leaf extracts and purified compound 3-O-p-coumaryl quinic acid (FIG. 1) obtained from leaf extract for treating CD33+ acute and chronic myeloid leukemia.

*Piper betel* leaves have a strong pungent aromatic flavour and are widely used in India as a masticatory. Generally, mature or overmature leaves, which have ceased growing but not yet become brittle are used for chewing. The basic preparation for chewing purposes consists of betel leaf smeared with hydrated lime and catechu to which scrapings of arecanut are added; flavourings such as coconut shavings, clove, cardamom, fennel, powdered liquorice, nutmeg and also tobacco are used according to one's taste. In some places prepared *Piper betel* leaf preparation is covered with silver or gold film. As a masticatory, it is credited with many properties: it is aromatic, digestive, stimulant and carminative. Medicinally it is useful in catarly and pulmonary infections; it is also uses for poultices. The effects of chewing of betel leaves with arecanut and other adjuncts are the excitation of the salivary glands and the irritation of the mucous membrane of the mouth. The red coloration produced is due to a pigment in the arecanut, which manifests itself under the action of alkali in lime and catchu. A mild degree of stimulation is produced, resulting in a sensation of warmth and well-being, besides imparting a pleasant odour. The most important factor determining the aromatic value of the leaf is the amount and particularly the nature of the essential oil present. Betel leaves from different regions vary in smell and taste. The most pungent is the Sanchi type, while the most wild and sweet ones are from Varansai. The betal leaves contain essential oils, the content of oil varies from 0.7 to 2.6 per cent depending upon the varieties of leaves. The oil consists of phenols and terpens. The higher the proportion of phenol the better the quality. An isomer of eugenol named chavibetol (betel phenol; 4-alkyl-2-hydroxy-1methoxy benzene) is considered to be characteristic constituent of betel oil. Betel oil of Indian types contains a predominant phenolic constitutent and used in the treatment of various respiratory problems, either as a local application or by gargle. It has carminative properties. It exhibits in different actions on the central nervous system of mammals. The essential oil and extracts of the leaves possess activity against several Gram-positive and Gram-negative bacteria such as *Micrococcus pyogenes* var. Albus, *Bacillus subtilis* and *B. Megaterium, Diplococcus pneumoniae, Streptococcus pyogenes, Escherichia coli, Salmonella typhosa, Vibrio comma, Shigella dysenteriae, Proteus vulgaris, Pseudomonas solanacaerum, Sarcina lutea* and *Erwinia carototora*. The essential oil and leaf extracts also showed anti-fungal activity against *Asperigillus niger* and *A. Oryzae, Curvularia lunata* and *Fusarium oxysporum*. The oil is found to be lethal in about 5 miutes to the protozoa, *Paramaeceum caudatum* (5). Steam-distillate of the leaves showed activity against *Mycobacterium tyberculosis*.

REFERENCES

1. Sawyers C L, The New England Journal of Medicine, 340 (17), 1330–1340, 1999.
2. Vitale, C; Romagnani, C, et al., Proc. Natl. Acd. Sci. USA, 96 (26), 15091–15096, 1999.
3. Vitale, C et al., Proc. Natl. Acd. Sci, USA, 98 (10), 5764–5769, 2001.
4. Sievers E L, Appelbaum, F R et al., Blood, 93, 3678–3684, 1999.

OBJECT OF THE INVENTION

The main object of the invention is to provide a new herbal-based composition for the treatment of CD33+ acute and chronic myeloid leukemia by *Piper betel* leaf extracts.

Another object of the invention is to provide a process for the isolation of active fractions from leaves or any of the plant parts of *Piper betel* to treat CD33+ AML and CML.

Still another object of the invention is to provide a simplified method of isolation of active components from all plant parts of *Piper betel* possessing biological activities relevant to the treatment of CD33+ AML and CML.

Yet another object of the invention is to provide a new herbal product from active fraction from leaves or any other plant parts of *Piper betel* for the treatment of CD33+ AML and CML.

Yet another object of the invention is to provide a herbal compound 3-O-p-coumaryl quinic acid purified from leaves of *Piper betel* for the treatment of CD33+ AML and CML.

Yet another object of the invention is to provide a process for the preparation of extract from leaves or any other plant parts of *Piper betel* for the treatment of CD33+ AML and CML.

Yet another object of the invention is to provide a simplified method of extract preparation from leaves or any other plant parts of *Piper betel* for the treatment of CD33+ AML and CML.

Yet another object of the invention is to provide a process for the preparation of 3-O-p-coumaryl quinic acid from leaves of *Piper betel* for the treatment of CD33+ AML and CML.

Yet another object of the invention is to provide a simplified method of preparation of 3-O-p-coumaryl quinic acid from all plant parts of *Piper betel* for the treatment of CD33+ AML and CML.

DESCRIPTION OF THE INVENTION

Accordingly, the present invention provides an herbal-based composition from *piper betle* leaves for the treatment of CD33+ acute and chronic myeloid leukemia.

Doses for myeloid leukemia patient depends on the in-vitro efficiency of the drug from piper betel either individually or in combination, the doses of in-vitro application for human myeloid cancer patients may range from 200 mg to 500 mg per day per patient if given as individual fraction (fraction 1 or fraction 9) or as a combination of fraction 1 and fraction 9 in the ratio between 0.1:5 to 5.0.1 preferably in the ratio 1:1 totaling 125 mg to 370 mg per day per patient through intravenous route.

In an embodiment of the invention relates to evaluation of bioactivity of fractions 1 to 9 isolated from *piper betel* leaf against cancer cells.

In an embodiment of the invention relates to evaluation of bioactivity of fractions 1 to 9 isolated from *piper betel* leaf for the treatment of CD33+ acute and chronic myeloid leukemia.

The invention also provides a process for isolation of 3-O-p-coumaryl quinic acid from *piper betel*, which is reported for the first time.

Another embodiment of the invention relates to a process for the isolation of active fractions from leaves or any other plant parts of *Piper betel* to treat CD33+ AML and CML.

Still another embodiment of the invention relates to a simplified method of isolation of active components from all plant parts of *Piper betel* possessing biological activities relevant to the treatment of CD33+ AML and CML.

Yet another embodiment of the invention relates to a new herbal composition/fraction from leaves or any other plant parts of *Piper betel* for the treatment of CD33+ AML and CML.

Yet another embodiment of the invention relates to new activity of compound 3-O-p-coumaryl quinic acid purified from leaves of *Piper betel* for the treatment of CD33+ AML and CML.

Yet another embodiment of the invention relates to a process for the preparation of extract from leaves or any other plant parts of *Piper betel* for the treatment of CD33+ AML and CML.

Yet another embodiment of the invention relates to simplified method of extract preparation from leaves or any other plant parts of *Piper betel* for the treatment of CD33+ AML and CML.

Yet another embodiment of the invention relates to a process for the preparation of 3-O-p-coumaryl quinic acid from leaves of *Piper betel* for the treatment of CD33+ AML and CML.

Yet another embodiment of the invention relates to a simplified method of preparation of 3-O-p-coumaryl quinic acid from all plant parts of *Piper betel* for the treatment of CD33+ AML and CML.

EXAMPLE 1

Collection of Plant Material

The leaves and all other plant parts of *Piper betel* were collected from the climber from different areas and West Bengal, India. A voucher specimen was deposited at the Deptt. of Medicinal Chemistry at the Indian Inst. of Chemical Biology, 4 Raja S. C. Mullick Road, Kolkata-700 032.

EXAMPLE 2

Fresh leaves 5.3 kgs of *Piper betel* is thoroughly washed with distilled water. Leaves are cut into small pieces. It is then homogenized with distilled water 1.5 liter in a mixture-blender. The extract was filtered through a fine cheese-cloth and the filtrate was collected. The plant material inside the cloth was again extracted with water (1000 ml). The extract was filtered in a similar way. This process of extraction was repeated three times. The combined extract was centrifuged to obtain a clear solution. The clear extract was lyophilized yielding a semi-solid mass 150 gms. The extract was then tested for biological activity.

A potion (10.02 gm) of the extract was fractionated on Sephadex LH-20 column chromatography. The column was eluted with water, water-methanol (1:1) and methanol as eluent to give three fractions, fractions 1–3, in the order of elution. The three fractions were then tested for biological activity.

The fraction-2 (designated as Fraction E) showed biological activity, i.e., destruction of myeloid cells in human patients' ex vivo blood. Thin layer chromatography of this fraction showed two spots having Rf. 0.50 and 0.41 in the solvent system n-butanol:acetic acid:water (13:3:5). The HPLC analysis of this fraction showed several peaks as in FIG. 1 using Intersil ODS-3 (4.6×250 mm) analytical column, with a solvent system methanol:water:acetic acid (23:76:1), having flow rate of 1.0 ml/min and detection at 280 nm. With the retention time 3.60, 8.60, 9.30, 11.50, 12.70, 16.40, 19.20, 20.00, 24.00 and 36.60 mins respectively.

Figure 2:
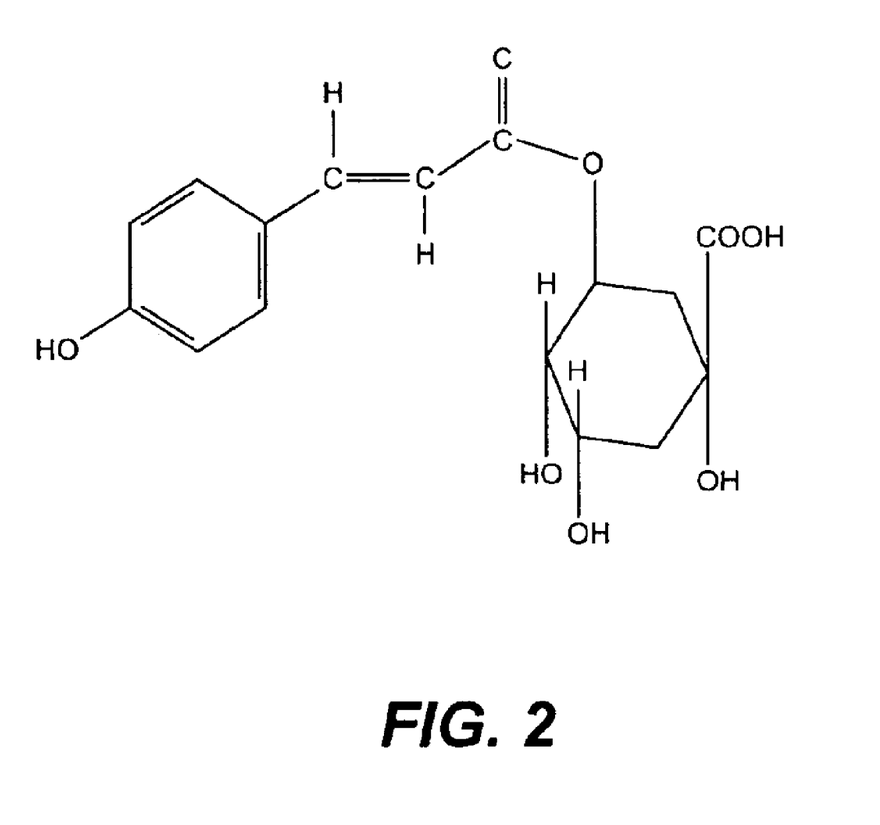
FIG. 2 represents structure of fraction 9 deduced as 3-O-p-coumaryl quinic acid.

Each peak of this fraction E was separated in a preparative HPLC using μ-Bonda pak column (19×300 mm), with a flow rate 12 ml/min and the detection at 280 nm. Compounds isolated from individual peak were tested for biological activity as described above. A purified compound was isolated from the peak having retention time 24.00 min. The structure of the compound was established as 3-O-p-coumaryl quinic acid (FIG. 2), mp. 245 to 247° C., $[\alpha]_D$ –75° (methanol).

| | |
|---|---|
| IR $\gamma^{KBr}_{max}$ cm$^{-1}$ | :3379 (OH), 1691 (CO), 1514, 1383, 1269, 1173 and 830 |
| $^1$H-NMR (CD$_3$OD) | 7.64 (1H, DJ = 15.9, H-7), 7.46 (2H, d, J = 8.4, H-2 and 6), 6.81 (2H, d, J = 8.4, H-3 and 5), 6.35 (1H, d, J = 15.9, H-8), 5.38 (1H, m, H-3), 4.19 (1H, br., H-4) 3.84 (1H, m, H-5), 2.2 (2H, br., H-2) and 2.0 (2H, br., H-6) |
| $^{13}$C-NMR (CD$_3$OD) | 176.00 (COOH), 167.65 (C-9), 160.24 (C-4), 145.68 (C-7), 130.17 (C-2 and 6), 126.25 (C-1), 115.81 (C-3 and 5), 75.16 (C-1'), 72.48, 70.98, 70.57, 37.79 and 37.22 |
| FAB MS m/z | 329 (M$^+$ + H), 361 (M$^+$ + Na), 377 (M$^+$ + K) |

EXAMPLE 3

The fresh leaves and all other plant parts of *Piper betel* (1.2 kg) was homogenized with methanol (800 ml) in a mixture-blender and then syndicated in an ultrasonic bath with 3 burst each for 15 min and allowed to be extracted over night for 16 HRs. Filtering through Whatman No. 1 filter paper separated the methanol-extracted material. The process of extraction was repeated for three times. The combined extract was evaporated to dryness in a flash evaporator under reduced pressure at 40° C. The residual substance was then dried under high vacuum and the semi-solid mass (35.22 gm) was tested for biological activity (as mentioned above).

The methanol extract (14 gm) was chromatographed on Diaion HP-20 (380 gm), elution being carried out with water, water-methanol (1:1) and methanol. Eluted three fractions were tested for biological activity.

HPTLC of water-methanol fraction (fraction E) showed similar Rf values (0.5 and 0.41) as described in example. Active compound, 3-O-p-coumaryl quinic acid was isolated from the fraction E by using preparative HPLC as described in example-2.

EXAMPLE 4

Preparation of peripheral blood mononuclear cells (PBMC) from CD33+ myeloid leukemia patients ex vivo blood.

Whole blood (10 ml) was drawn from a previously diagnosed CD33+ myeloid leukemic patient and mononuclear cells were separated by Ficoll/hypaqal density gradient centrifugation.

EXAMPLE 5

PBMC from CD33$^-$ myeloid leukemia patients. Whole blood (10 ml) was drawn from a previously diagnosed CD33$^-$ myeloid leukemia patient. Mononuclear cells were separated by Ficoll/hypaque density gradient centrifugation.

EXAMPLE 6

Incubation of PBMC of myeloid leukemia patients with crude *Piper betel* extract. PBMC (2×10$^6$/ml) of myeloid leukemia patients were incubated with *Piper betel* extract (10.0 mg/ml) for 48 hours and then washed and counted for viability.

EXAMPLE 7

Incubation of PBMC of myeloid leukemia patients with fraction E in vitro. PBMC (2×10$^6$/ml) of myeloid leukemia patients were incubated with varied concentrations of fraction E for 48 hours. Cells were then washed and counted for viability.

EXAMPLE 8

Incubation of PBMC of myeloid leukemia patients with purified compound 3-O-p-coumaryl quinic acid in vitro. PBMC (2×10$^6$/ml) of myeloid leukemia patients were incubated with varied concentrations of purified compound for 48 h. Cells were then washed, and counted for viability.

EXAMPLE 9

Flow cytometry of myeloid leukemia cells. Myeloid leukemia cells before and after in vitro incubation with crude *Piper betel* extract, purified fraction E or purified 3-O-p-coumaryl quinic acid were marked with anti-CD33-FITC and anti-CD13-PE monoclonal antibodies. Cells were then analysed in a flow cytometer (FACS Calibur, Bection Dickinson, USA)

EXAMPLE 10

Incubation of myeloid leukemic cells with fractions having retention time 3.60 (fraction-1) and 24.00 min (fraction 9). PBMC of myeloid leukemic patients were incubated with above-mentioned fractions, alone or in combination of the two for 48 HRs. Cells were then washed and counted for viability.

Results of the Experiments

Figure 3:
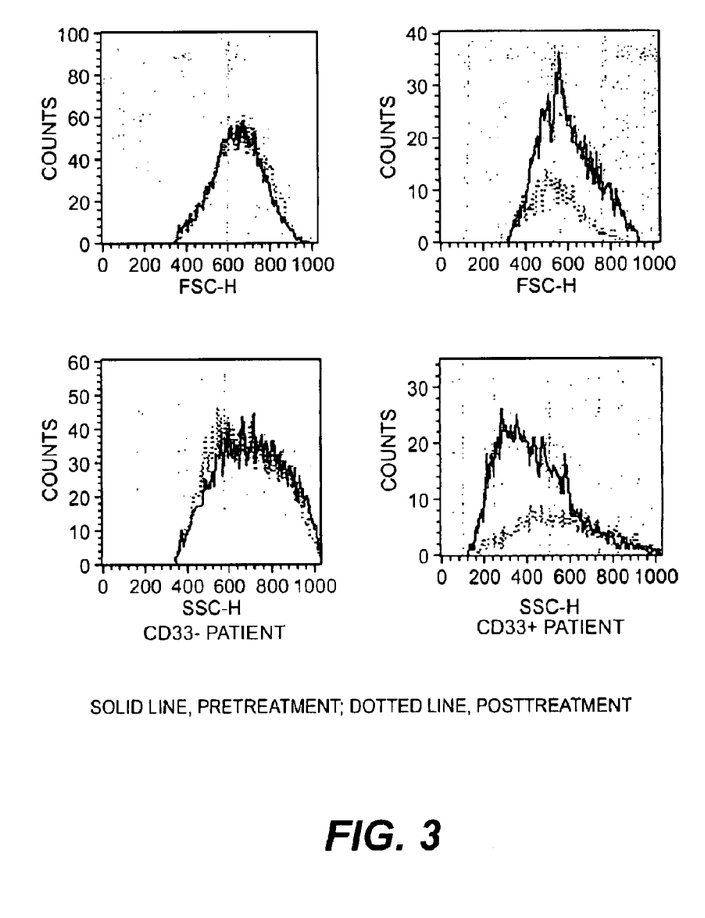
FIG. 3 represents destruction of CD33+ myeloid leukemia cells in vitro by *P.Betel* leaf extract as demonstrated by flow cytometry. Data is presented as histograms. In upper panels, Forward Scattering of light (X-axis) is plotted against the cell numbers (counts Y-axis). In the lower panels, side scattering of light (X-axis) is plotted against the cell numbers. Solid lines represent data with myeloid leukemia cells before treatment with *P.betel* leaf extract and the dotted lines represent data with myeloid leukemiccells after treatment with *P.betel* leaf extract (10.0 mg/ml) for 48 hours.

Results of Example 6:

As shown in FIG. 3, CD33+ myeloid leukemia cells were killed in the presence of crude *Piper betel* extract. On the other hand, crude *Piper betel* extract has no effect on the CD33$^-$ myeloid leukemic cells.

Figure 4:
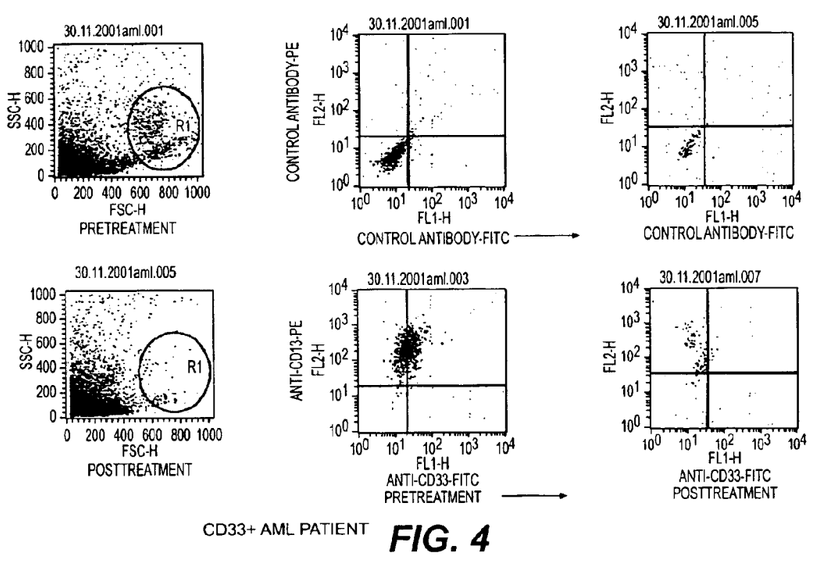
FIG. 4 represents destruction of $CD33^+$ myeloid leukemic cells in vitro by fraction E as demonstrated by flow cytometry. Dot plots of Forward Scatter vs. Side Scatter with $CD33^+$ myeloid leukemic cells before and after treatment with fraction E (100.0 µg/ml) for 48 hours are shown in left panels where gated region (R1) represents myeloid leukemic cells. Two colour dot plots are also shown after staining with fluorescein isothiocyanate (FITC) conjugated anti-CD33 and phycocrytbrin (PE) conjugated anti-CD13 monoclonal antibodies. Isotype matched control antibodies (FITC and PE conjugated) were used as negative controls. Upper left quadrants represented CD13, $CD33^+$ cells and upper right quadrants represented $CD13^+$, $CD33^+$ cells.
Figure 5:
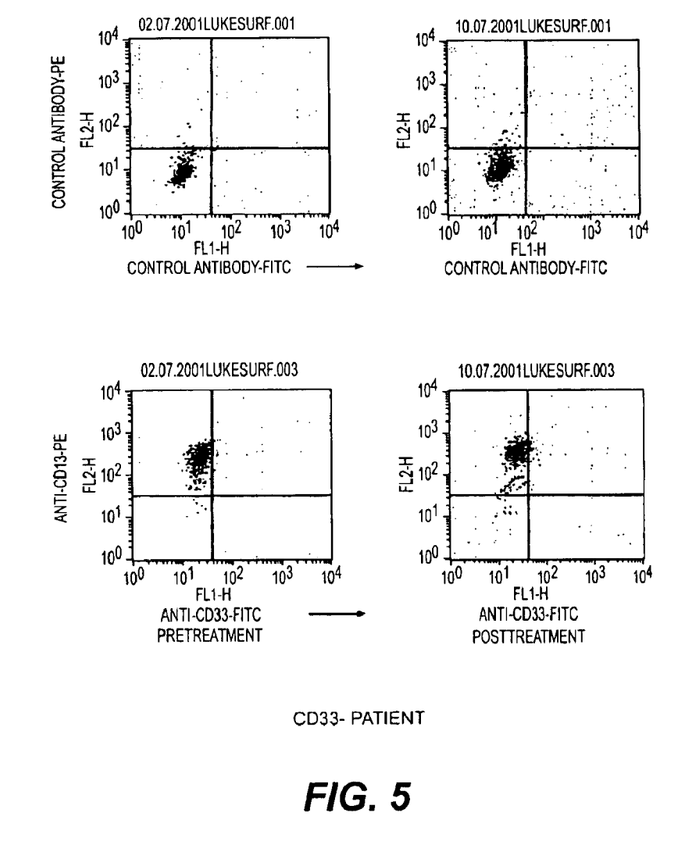
FIG. 5 represents $CD33^-$ myeloid leukemiccells are unaffected by fraction E as demonstrated by flow cytometry. Two colour dot plots after staining $CD33^-$ myeloid leukemic cells with anti-CD33-FITC and anti-CD13-PE monoclonal antibodies before and after treatment with fraction E (100.0 µg/ml) for 48 hours are shown. Isotype matched control monoclonal antibodies (FITC and PE labelled) were used as negative controls. Upper left quadrants represented $CD13^+$, CD33 cells and upper right quadrants represented $CD13^+$, $CD33^+$ cells.
Figure 6:
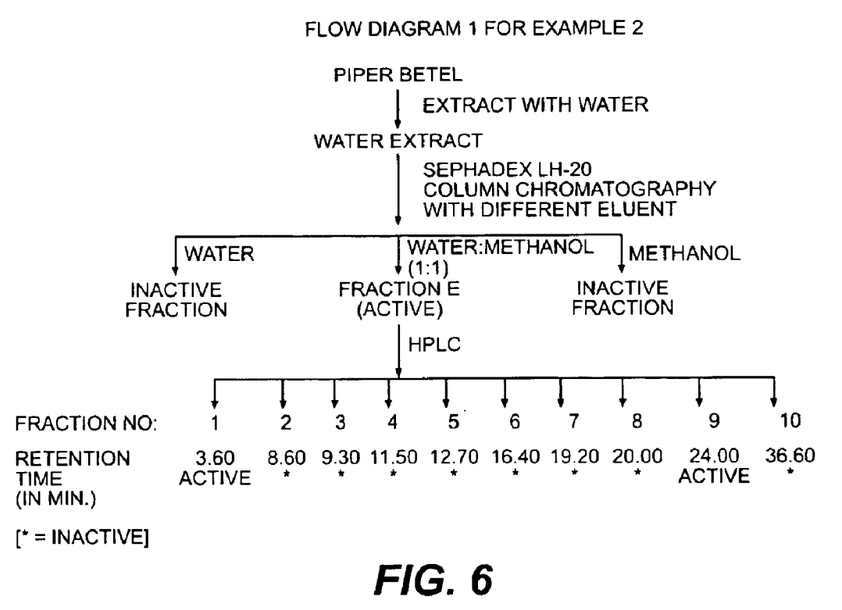
FIG. 6 represents flow diagram for example 2
Figure 7:
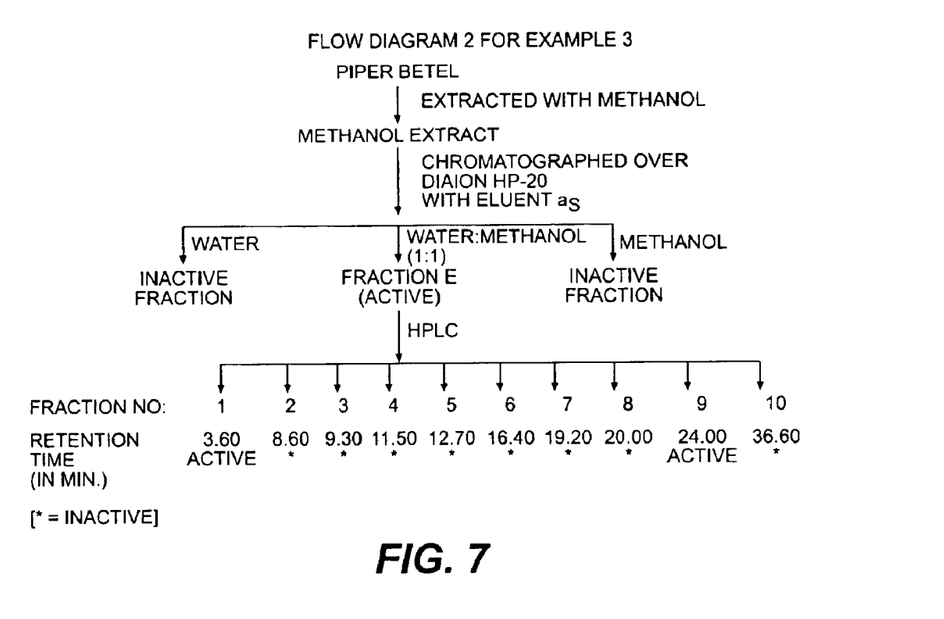
FIG. 7 represents flow diagram for example 3

Results of Examples 7, 8 and 9:

As shown in FIG. 4, CD33+ myeloid leukemia cells are destroyed by fraction E. On the other hand, CD33$^-$ myeloid leukemia cells remained unaffected. (FIG. 5). PBMC of CD33+ myeloid leukemia patients (both AML and CML) are destroyed by purified compound 3-O-p-coumaryl quinic acid (Table -1).

Results of Example 10:

As shown in Table 2 combining fractions of 1 and 9 produced greater effects as compared to their individual activity at lower concentration.

TABLE 1

Growth inhibition of AML and CML cells in vitro by purified compound

| | Percent inhibition of growth by purified compound 3-O-p-coumaryl quinic acid | |
|---|---|---|
| Type of myeloid leukemia | 100 μg/ml | 600 μg/ml |
| AML | 53.37 | 100.00 |
| CML | 2.53 | 79.50 |

TABLE 2

Growth inhibition of AML cells in vitro by fractions 1 and 9

| Type of myeloid leukemia | Fractions | Doses (μg/ml) | % Inhibition |
| --- | --- | --- | --- |
| AML | 1 | 100 | 79.50 |
| | 9 | 100 | 54.00 |
| | 1 + 9 | 50 + 50 | 100.00 |

We claim:

1. A method of treating either CD33+ acute myeloid leukemia or CD33+ chronic myeloid leukemia by administering a pharmaceutically effective amount of compound 3-O-p-coumaryl quinic acid to a subject in need thereof.

2. A method as claimed in claim 1, wherein the compound has 100% activity against CD33+ chronic myeloid leukemia.

3. A method as claimed in claim 1, wherein the compound has 85% activity against CD33+ chronic myeloid leukemia.

4. A method as claimed in claim 1, wherein the subject is an animal.

5. A method as claimed in claim 1, wherein the subject is a human being.

6. A method as claimed in claim 1, wherein the administering is intravenous.

* * * * *